United States Patent
Jahns et al.

(10) Patent No.: US 10,792,228 B2
(45) Date of Patent: Oct. 6, 2020

(54) KIT OF PARTS FOR PRODUCING A GLASS IONOMER CEMENT, PROCESS OF PRODUCTION AND USE THEREOF

(71) Applicant: 3M INNOVATIVE PROPERTIES COMPANY, St. Paul, MN (US)

(72) Inventors: Michael Jahns, Gilching (DE); Markus Mikulla, Andrechs-Frieding (DE); Robert F. Peez, Landsberg (DE); Adrian S. Eckert, Herrsching (DE); Rainer A. Guggenberger, Herrsching (DE); Simone Raynoschek, Neuss (DE); Afshin Falsafi, Woodbury, MN (US); Bradley D. Craig, Lake Elmo, MN (US); Jimmie R. Baran, Jr., Prescott, WI (US); Joel D. Oxman, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 97 days.

(21) Appl. No.: 15/775,040

(22) PCT Filed: Oct. 11, 2016

(86) PCT No.: PCT/US2016/056366
§ 371 (c)(1),
(2) Date: May 10, 2018

(87) PCT Pub. No.: WO2017/083039
PCT Pub. Date: May 18, 2017

(65) Prior Publication Data
US 2019/0000723 A1 Jan. 3, 2019

(30) Foreign Application Priority Data
Nov. 11, 2015 (EP) .................................... 15194008

(51) Int. Cl.
| | | |
|---|---|---|
| *A61K 6/08* | (2006.01) | |
| *A61K 6/889* | (2020.01) | |
| *A61K 6/15* | (2020.01) | |
| *A61K 6/62* | (2020.01) | |
| *A61K 6/71* | (2020.01) | |
| *A61K 6/75* | (2020.01) | |
| *A61K 6/76* | (2020.01) | |
| *A61K 6/77* | (2020.01) | |

(52) U.S. Cl.
CPC ................ *A61K 6/889* (2020.01); *A61K 6/15* (2020.01); *A61K 6/62* (2020.01); *A61K 6/71* (2020.01); *A61K 6/75* (2020.01); *A61K 6/76* (2020.01); *A61K 6/77* (2020.01)

(58) Field of Classification Search
CPC ............................. A61K 6/0835; A61K 6/889
See application file for complete search history.

(56) References Cited

U.S. PATENT DOCUMENTS

| | | | |
|---|---|---|---|
| 4,209,434 A | 6/1980 | Wilson | |
| 4,360,605 A | 11/1982 | Schmitt | |
| 4,376,835 A | 3/1983 | Schmitt | |
| 4,569,954 A | 2/1986 | Wilson | |
| 4,941,751 A | 7/1990 | Muehlbauer | |
| 5,088,830 A | 2/1992 | Muehlbauer | |
| 5,520,922 A | 5/1996 | Gasser | |
| 5,936,006 A | 8/1999 | Rheinberger | |
| 6,386,872 B1 | 5/2002 | Mukasa | |
| 6,437,019 B1 * | 8/2002 | Rusin ................... | A61K 6/0017 523/117 |
| 6,543,611 B1 | 4/2003 | Peuker | |
| 6,715,645 B2 | 4/2004 | Peuker | |
| 6,719,834 B1 | 4/2004 | Braun | |
| 7,156,911 B2 | 1/2007 | Kangas | |
| 7,393,882 B2 | 7/2008 | Wu | |
| 9,220,578 B2 | 12/2015 | Peuker | |

(Continued)

FOREIGN PATENT DOCUMENTS

| | | |
|---|---|---|
| EP | 0783872 | 7/1997 |
| EP | 2228049 | 9/2010 |
| EP | 2316407 | 5/2011 |

(Continued)

OTHER PUBLICATIONS

Hill, R.G., et al., "A Rheological Study of the Role of Additives on the Setting of Glass-ionomer Cements," J Dent Res 67(12): 1446-1450, Dec. 1998, pp. 1446-1450.

(Continued)

*Primary Examiner* — Michael F Pepitone

(57) ABSTRACT

The invention relates to a kit of parts for preparing a glass ionomer composition for dental use, the kit of parts comprising a Powder Part P and a Liquid Part L, Powder Part P comprising: acid-reactive inorganic filler, Liquid Part L comprising: water, complexing agent, polyacid, either the Powder Part P or the Liquid Part L or the Powder Part P and the Liquid Part L comprising non-aggregated nano-sized particles based on silica or alumina, the composition obtained by combining the components of Powder Part P and Liquid Part L before hardening comprising the components in the following amounts: non-aggregated nano-sized particles: from 0.1 to 15 wt.-%, acid-reactive filler in an amount from 50 to 75 wt.-%, polyacid: 7 to 20 wt.-%, complexing agent: 0.5 to 3 wt.-%, water: 5 to 18 wt.-%, wt.-% with respect to the weight of the whole composition.

15 Claims, No Drawings

(56) References Cited

U.S. PATENT DOCUMENTS

2005/0252413 A1  11/2005  Kangas
2005/0256223 A1  11/2005  Kolb

FOREIGN PATENT DOCUMENTS

| JP | H04-97929 | 3/1992 |
| JP | 2002-275017 | 9/2002 |
| JP | 2007-91689 | 4/2007 |
| RU | 2010108567 | 9/2011 |
| WO | WO 2015-088956 | 6/2015 |

OTHER PUBLICATIONS

Klapdohr, "New Inorganic Components for Dental Filling Composites", An International Journal of Chemistry, 2005, vol. 136, No. 01, pp. 21-45, XP01937868.
Moszner, "Nanotechnology for Dental Composites", International Journal of Nanotechnology, 2004, vol. 01, No. 1/2, pp. 130-156, XP008049452.
International Search Report for PCT International Application No. PCT/US2016/056366, dated Nov. 22, 2016, 5 pages.

* cited by examiner

KIT OF PARTS FOR PRODUCING A GLASS IONOMER CEMENT, PROCESS OF PRODUCTION AND USE THEREOF

CROSS REFERENCE TO RELATED APPLICATIONS

This application is the § 371 U.S. National Stage of International Application No. PCT/US2016/056366, filed 11 Oct. 2016, which claims the benefit of European Patent Application No. 15194008.7, filed 11 Nov. 2015, the disclosures of which are incorporated by reference herein in their entireties.

FIELD OF THE INVENTION

The invention relates to a kit of parts for producing a glass ionomer composition, wherein the cement is obtainable by mixing a powder and a liquid part. The glass ionomer composition is in particular useful as or for producing dental luting cement, dental filling material, dental core build up material, dental liner or dental root channel filling material.

BACKGROUND ART

Glass ionomer cements have been used for more than 30 years for dental restorative treatments.

Typically glass ionomer cements are reacted by mixing a powder part with a liquid part.

The powder component typically comprises as essential or important component an acid-reactive filler (e.g. a fluoro alumino silicate glass).

The liquid component typically comprises as essential components water, polycarboxylic acid and a complexing or chelating agent (e.g. tartaric acid) for adjusting the setting properties.

Main advantages of glass ionomer cements are said to be self-adhesion to tooth structure, fluoride release and the ability to be placed in one part (bulk-fill).

One disadvantage reported by some practitioners is the brittle nature and relatively low physical-mechanical properties of the glass ionomer cement compared to the physical-mechanical properties reported for resin-based composite filling materials.

There have been various approaches to improve especially the flexural strength of glass ionomer cements.

E.g. it is reported that by increasing the overall content of polycarboxylic acid in comparison to the acid-reactive filler, the flexural strength can be improved.

However, by increasing the amount of polycarboxylic acid contained in the liquid part, the liquid part became too viscous making it nearly impossible to adequately mix the powder and liquid component.

To overcome this issue, it was suggested to put a part of the polycarboxylic acid in dry form into the powder component.

By doing this, however, it was realized that the storage stability of the product is sometimes negatively affected. Over time, humidity being present in the air may start to migrate into the powder component causing a glass ionomer reaction to start at least partially.

In order to overcome the susceptibility of the powder part to ambient humidity, encapsulating at least parts of the powder component was considered.

However, encapsulating particles is often not easy and may affect the overall reactivity of the encapsulated powder.

Another disadvantage reported by some practitioners is the difficulty to homogenously mix the powder and liquid compositions.

To achieve certain physical mechanical properties (like flexural strength and/or compressive strength), the glass ionomer cement typically needs to have a certain content of filler.

However, increasing the amount of filler in the powder part often results in difficulties during the preparation of the glass ionomer composition if the powder and liquid part are mixed.

The more viscous the composition becomes, the more difficulties typically arise during mixing.

Thus, from a mixing point of view a low viscous composition is desired.

However, a low viscous composition often does not show the desired physical mechanical properties after hardening.

U.S. Pat. No. 4,376,835 (Schmitt et al.) describes a calcium aluminum fluorosilicate glass powder, wherein the calcium in the surface of the powder's particles is depleted. The glass powder may be prepared by surface treating calcium aluminum fluorosilicate powder particles with an acid which forms calcium salts, washing the calcium salts off the treated particles and drying the washed particles. Cements formed from the glass powder exhibit reduced periods of water sensitivity, while permitting sufficient time of processing.

U.S. Pat. No. 6,719,834 (Braun et al.) relates to a polyelectrolyte cement containing at least two reaction partners: a) at least one metal-cation-releasing compound and b) one or more polyelectrolyte capable of being converted into a solid state, wherein at least one of the polyelectrolytes is at least partially water soluble and wherein at least a part of the reaction partners (a) and/or (b) is coated with an organic surface-coating agent. The polyelectrolyte cement is stable in storage and can be easily mixed.

JP 2002-275017 describes a material for preparing dental glass ionomer cements. The powdery material comprises 10-50 wt.-% of fluoroaluminosilicate glass powder, less or equal than 10 wt.-% of a powder selected from certain oxides, with the balance of a powdery inert filler. Due to a reduced content of fluoroaluminosilicate glass powder (10 to 50 wt.-%), the glass ionomer cement is said to be excellent in temporarily adhesive and temporarily sealing use, i.e. has reduced mechanical properties. Compressive strength values in the range of less than 70 MPa are reported.

U.S. Pat. No. 5,520,922 (Gasser et al.) relates to a filling material for dental root canals comprising (A) 25-80 wt.-% glass ionomer cement containing (a) an aluminium fluorosilicate glass, (b) a certain polymeric polyacid, (c) water and (B) 25-75 wt.-% of a fluoride and/or oxide of heavy metal elements.

RU 2010/108567 A describes a glass ionomer cement containing a powder and a liquid, wherein 0.015 to 0.025% of silicon nano particles have been added to the powder. It is stated that the obtained cement provides better adhesion, has improved strength and oral fluid stability.

US 2005/0252413 A1 (Kangas et al.) relates to hardenable dental or orthodontic compositions filled with nanosized particles. More specifically, an ionomer and resin modified ionomer composition containing nano filler is described.

US 2005/0256223 A1 (Kolb et al.) describes hardenable dental or orthodontic compositions filled with zirconia nano particles. More specifically, an ionomer and resin modified ionomer composition containing nano zirconia filler is described.

WO 2015/088956 A1 (3M IPC) relates to a kit of parts for preparing a glass ionomer cement, wherein the kit comprises a part A and a part B, part A being a powder and comprising an acid-reactive inorganic filler in a certain amount and having a mean particle size in the range of 3.5 to 10 µm, a non acid-reactive filler in a certain amount and having a mean particle size in the range of 1.0 to 3.5 µm, part A not comprising polyacid in an amount above 1 wt. %, part B being a liquid and comprising a polyacid in a certain amount, water and a complexing agent.

In Int. J. of Nanotechnology, Vo. 1, Nos. ½, 2014, page 144 it is described that with respect to dental composite materials the thickening effect can be avoided by utilizing very small monodisperse particles, e.g. below 100 nm, with very favourable surface modification to inhibit agglomeration and to adapt the surface to the matrix resin. Surface modification is typically performed with MPTMS in moisture or in solution in the presence of water.

Thus, there is still room for improvement especially with regard to the requirements to be fulfilled with respect to modern dental materials.

DESCRIPTION OF THE INVENTION

It is an object of the invention to provide a glass ionomer composition (GI), which can be mixed easily (either manually or by using electrically driven mixing devices). It would also be desirable, if the obtained glass ionomer composition shows adequate physical mechanical properties (like flexural and/or compressive strength) after mixing and hardening.

This object can be achieved, by the kit of parts and the composition obtained when mixing the powder and liquid part of the kit of parts as described in the present text.

In one embodiment the present invention features a kit of parts for preparing a glass ionomer composition for dental use,
the kit of parts comprising a Powder Part P and a Liquid Part L,
  Powder Part P comprising
  acid-reactive inorganic filler,
  Liquid Part L comprising
  water,
  complexing agent,
  polyacid,
either the Powder Part P or the Liquid Part L or the Powder Part P and the Liquid Part L comprising non-aggregated nano-sized particles based on silica or alumina, the composition obtained by combining the components of Powder Part P and Liquid Part L before hardening comprising the components in the following amounts:
  non-aggregated nano-sized particles: from 0.1 to 15 wt.-%,
    acid-reactive filler in an amount from 50 to 75 wt.-%,
    polyacid: 7 to 20 wt.-%,
    complexing agent: 0.5 to 3 wt.-%,
    water: 5 to 18 wt.-%,
    wt.-% with respect to the weight of the whole composition.

The invention is also directed to a composition obtainable or obtained by combining the components contained in Powder Part P and Liquid Part L of the kit of parts described in the present text.

A further aspect of the invention is directed to a delivery system comprising Compartment A and Compartment B, Compartment A containing Powder Part P and Compartment B containing Liquid Part L, the delivery system having the shape of a dental capsule.

Yet a further aspect of the invention is directed to the use of non-aggregated nano-particles for reducing the viscosity of a composition obtainable by mixing the components of a Powder Part P and a Liquid Part L as described in the present text.

Unless defined differently, for this description the following terms shall have the given meaning:

A "dental composition" or a "composition for dental use" or a "composition to be used in the dental field" is any composition which can and is to be used in the dental field. In this respect the composition should be not detrimental to the patients' health and thus free of hazardous and toxic components being able to migrate out of the composition. Dental compositions are typically hardenable compositions, which can be hardened at ambient conditions, including a temperature range from about 15 to 50° C. or from about 20 to 40° C. within a time frame of about 30 min or 20 min or 10 min. Higher temperatures are not recommended as they might cause pain to the patient and may be detrimental to the patient's health. Dental compositions are typically provided to the practitioner in comparable small volumes, that is volumes in the range from about 0.1 to about 100 ml or from about 0.5 to about 50 ml or from about 1 to about 30 ml. Thus, the storage volume of useful packaging devices is within these ranges.

A "radically polymerizable component" is any component which can be cured or solidified e.g. by heating to cause polymerization or chemical crosslinking, or e.g. by radiation-induced polymerization or crosslinking, or e.g. using a redox initiator or by any other radical forming process. A radically polymerizable component may contain only one, two, three or more radically polymerizable groups. Typical examples of radically polymerizable groups include unsaturated carbon groups, such as a vinyl group being present e.g. in a (methyl)acrylate group.

The cement composition described in the present text does not contain radically polymerizable components in an amount above about 0.5 or 1 wt.-% with respect to the whole composition. The cement composition described in the present text is essentially free of radically polymerizable components bearing (meth)acrylate groups.

A "monomer" is any chemical substance which can be characterized by a chemical formula, bearing radically polymerizable unsaturated groups (including (meth)acrylate groups) which can be polymerized to oligomers or polymers thereby increasing the molecular weight. The molecular weight of monomers can usually simply be calculated based on the chemical formula given.

As used herein, "(meth)acryl" is a shorthand term referring to "acryl" and/or "methacryl". For example, a "(meth)acryloxy" group is a shorthand term referring to either an acryloxy group (i. e., $CH_2=CH-C(O)-O-$) and/or a methacryloxy group (i. e., $CH_2=C(CH_3)-C(O)-O-$).

An "initiator" is a substance being able to start or initiate the curing process of radically polymerizable components or monomers, e.g. redox/auto-cure chemical reaction or by a radiation induced reaction or by a heat induced reaction.

A "powder" means a dry, bulk solid composed of a large number of very fine particles that may flow freely when shaken or tilted.

A "particle" means a substance being a solid having a shape which can be geometrically determined. Particles can typically be analysed with respect to e.g. grain size or diameter.

The mean particle size of a powder can be obtained from the cumulative curve of the grain size distribution and is defined as the arithmetic average of the measured grain sizes of a certain powder mixture. Respective measurements can be done using commercially available granulometers (e.g. CILAS Laser Diffraction Particle Size Analysis Instrument).

The term "d50/μm" with regard to particle size measurement means that 50% of the particles in the analyzed volume have a size below x μm. E.g., a particle size value of below 100 μm (d50) means that within the analyzed volume, 50% of the particles have a size below 100 μm.

"Nano-sized particles" shall mean particles having a mean particle size in the range of 5 to 500 nm or 5 to 300 nm or 5 to 200 nm. For spherical particles, "size" refers to the diameter of the particle. For non-spherical particles, "size" refers to the so called "equivalent spherical diameter" which is the diameter of a sphere of equivalent volume.

The term "primary particle size" refers to the size of a non-associated single particle. X-ray Diffraction (XRD) is typically used to measure the primary particle size using the techniques described herein.

The term "associated" refers to a grouping of two or more primary particles that are aggregated and/or agglomerated. Similarly, the term "non-associated" refers to two or more primary particles that are free or substantially free from aggregation and/or agglomeration.

The term "aggregation" refers to a strong association of two or more primary particles. For example, the primary particles may be chemically bound to one another. The breakdown of aggregates into smaller particles (e.g., primary particles) is generally difficult to achieve.
Aggregated fillers are commercially available e.g. from Degussa, Cabot Corp or Wacker under the product designation Aerosil™, CAB-O-SIL™ and HDK (e.g. fumed or pyrogenic silica).

"Non-aggregated filler" means that the filler particles are present in a discrete, un-associated (i.e. non-agglomerated and non-aggregated) stage. If desired this can be proven by TEM microscopy. However, unavoidable traces of small amounts of agglomerated or aggregated particles (e.g. up to about 1% compared to the amount of non-aggregated filler) may still be there.

Non-aggregated nano-sized silicas are commercially available e.g. from Nalco Chemical Co. (Naperville, Ill.) under the product designation NALCO COLLOIDAL SILICAS e.g. NALCO products #1040, 1042, 1050, 1060, 2327 and 2329. Non-aggregated fillers are used and described e.g. in U.S. Pat. No. 7,393,882 (3M). The content of this reference is herewith incorporated by reference.

The term "agglomeration" refers to a weak association of two or more primary particles. For example, the primary particles may be held together by charge or polarity. The breakdown of agglomerates into smaller particles (e.g., primary particles) is less difficult than the breakdown of aggregates into smaller particles.

"Paste" shall mean a soft, viscous mass of solids dispersed in a liquid. "Viscous" means a viscosity above about 3 Pa*s (at 23° C.).

A "solvent" means a liquid which is able to at least partially disperse or dissolve a component at ambient conditions (e.g. 23° C.). A solvent typically has a viscosity below about 10 or below about 8 or below about 6 Pa*s.

"Glass ionomer cement" or "GIC" shall mean a cement curing or hardening by the reaction between an acid-reactive glass and a polyacid in the presence of water.

"Resin modified glass ionomer cement" or "RM-GIC" shall mean a GIC containing in addition radically polymerizable component(s), an initiator system and typically 2-hydroxyl-ethyl-methacrylate (HEMA).

The kit of parts described in the present text relates to a glass ionomer cement, but not to a resin modified glass ionomer cement.

"Acid-reactive filler" shall mean a filler that chemically reacts in the presence of an acidic component.

"Non acid-reactive filler" shall mean a filler, which does not show a chemical reaction within 6 min at all, if mixed with a (poly)acid or which shows only a reduced (i.e. time-delayed) reaction.

To distinguish an acid-reactive filler from a non acid-reactive filler the following test can or is to be conducted:
A composition is prepared by mixing Part A with Part B in a mass ratio of 3 to 1, wherein:
Part A contains: filler to be analyzed: 100 wt.-%.
Part B contains: poly (acrylic acid co maleic acid) (Mw: about 18,000+/−3,000): 43.6 wt.-%, water: 47.2 wt.-%, tartaric acid: 9.1 wt.-%, benzoic acid: 0.1 wt.-%.

The filler is characterized as non-acid reactive, if within 6 min after preparing the above composition the shear stress is less than 50,000 Pa, if determined by conducting an oscillating measurement using a rheometer by applying the following conditions: using an 8 mm plate, 0.75 mm gap, at 28° C., frequency: 1.25 Hz, deformation: 1.75%.

"Cation reduced aluminosilicate glasses" shall mean a glass having a lower content of cations in the surface region of the glass particle compared with the inner region of the glass particle.

These glasses react much slower upon contact with a solution of polyacrylic acid in water as compared to typical acid-reactive fillers. Examples of non acid-reactive fillers include quartz glass. Further examples are given in the text below.

Cation reduction can be achieved by a surface treatment of the glass particles. Suitable surface treatments include, but are not limited to, acid washing (e.g., treatment with a phosphoric acid or with hydrochloric acid), treatment with a phosphate or treatment with a chelating agent such as tartaric acid.

"Polyacid" or "polyalkenoic acid" shall mean a polymer having a plurality of acidic repeating units (e.g. more than 10 or more than 20 or more than 50). That is, the acidic repeating units are attached to or pending from the backbone of the polymer.

"Complexing agent" or "chelating agent" shall mean a low molecular agent comprising moieties and being able to form a complex with metal ions like calcium or magnesium; e.g. tartaric acid. The terms "complexing agent" and "chelating agent" are interchangeable.

A "storage stable composition" is a composition which can be stored for an adequate period of time (e.g. at least about 12 months under ambient conditions) without showing significant performance issues (e.g. reduced flexural or compressive strength and/or which does not harden in the desired period of time (e.g. setting time greater than 6 min)) when used. A suitable test for determining the storage stability is given in the Example section below.

By "hardenable" or "curable" is meant that the composition can be cured or solidified, e.g. by conducting a glass ionomer cement reaction without the need for an additional curing system like chemical cross-linking, radiation-induced polymerization or crosslinking.

A composition is "essentially or substantially free of" a certain component, if the composition does not contain said component as an essential feature. Thus, said component is not willfully added to the composition either as such or in combination with other components or ingredient of other components.

A composition being essentially free of a certain component usually contains the component in an amount of less than about 1 wt.-% or less than about 0.5 wt.-% or less than about 0.1 wt.-% or less than about 0.01 wt.-% with respect to the whole composition or material. The composition may not contain the said component at all. However, sometimes the presence of a small amount of the said component is not avoidable e.g. due to impurities contained in the raw materials used.

"Ambient conditions" mean the conditions which the inventive composition is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are adjusted to about 23° C. and about 1013 mbar. In the dental and orthodontic field ambient conditions are reasonably understood as a pressure of about 950 to about 1050 mbar, temperature of about 15 to about 40° C. and relative humidity of about 20 to about 80%.

As used herein, "a", "an", "the", "at least one" and "one or more" are used interchangeably. The terms "comprises" or "contains" and variations thereof do not have a limiting meaning where these terms appear in the description and claims. The term "comprising" also includes the more limited expressions "consisting essentially of" and "consisting of".

Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and so forth used in the specification and claims are to be understood as being modified in all instances by the term "about."

The kit of parts described in the present text comprises a Powder Part P and a Liquid Part L. Upon mixing the components contained in those two parts, a composition in the form of a paste is obtained. That composition hardens by a so-called glass ionomer reaction.

As outlined above, the hand-mixing procedure to prepare glass ionomer composition is said to be often quite tedious.

This is especially the case with glass ionomer compositions for use in dental restorative applications, because the content of solid components (e.g., the ionomer glass) has to be high in order to achieve the desired physical mechanical properties. As a result, the obtained paste usually has a high viscosity which makes the final stage of the hand-mixing procedure difficult.

It was found that by using the kit of parts described in the present text, the viscosity of the pasty composition obtained when the Powder Part P and Liquid Part L are mixed is comparably low despite an overall high filler content. The viscosity of the obtained paste could be lowered by adding nano-sized particles to either the Powder Part P or the Liquid Part L, in particular to the Liquid Part L.

By doing so, the obtained composition contains a more optimized particle size distribution, allowing for a high content of fillers at a low viscosity.

This is not only beneficial if the composition is to be prepared by manually mixing the Powder Part P and Liquid Part L but also if the mixing is done using an electrically driven mixing device.

Further, if the kit of parts is stored in a dental mixing capsule, the prepared glass ionomer composition can be expressed out of this capsule more easily, as well (e.g. by applying less force).

Alternatively or in addition a dental mixing capsule can be used having a nozzle with a smaller diameter for delivering the composition to a surface. This can be helpful for delivering the paste more accurately e.g. into an oral cavity.

Thus, the kit of parts described in the present text enables the skilled person to provide a glass ionomer cement composition having superior handling properties.

The kit of parts described in the present text comprises a Powder Part P.

Powder Part P contains an acid-reactive inorganic filler.

The nature and structure of the acid-reactive inorganic filler is not particularly limited unless the desired result cannot be achieved. The acid-reactive inorganic filler has to be able to undergo a glass-ionomer reaction if reacted with a polyacid in the presence of water.

According to one embodiment, the acid-reactive inorganic filler can be characterized by at least one or more or all of the following parameters:

Mean particle size: about 3 to about 10 μm;
(d10/μm): from 0.5 μm to 3 μm; (d50/μm): from 2 μm to 7 μm; (d90/μm): from 6 μm to 15 μm.

If the mean particle size of the acid-reactive inorganic filler is above the range outlined above, the consistency of the composition obtained when mixing the compositions contained in the kit of parts described in the present text will not be adequate and the desired mechanical properties might be negatively affected.

If the mean particle size of the acid-reactive inorganic filler is below the range outlined above, the setting time will be too fast.

Suitable acid-reactive inorganic fillers include metal oxides, metal hydroxides, hydroxyapatite or acid-reactive glasses.

Typical metal oxides include barium oxide, strontium oxide, magnesium oxide, zinc oxide, lanthanum oxide, yttrium oxide and mixtures thereof.

Typical metal hydroxides include calcium hydroxide, magnesium hydroxide, strontium hydroxide, calcium hydroxide, lanthanum hydroxide, yttrium hydroxide and mixtures thereof.

Typical acid-reactive glasses include aluminosilicate glasses and in particular fluoroaluminosilicate ("FAS") glasses.

FAS glasses are particularly preferred. The FAS glass typically contains a sufficient amount of elutable cations so that a hardened dental composition can be obtained when the glass is mixed with the other components of the hardenable composition.

The FAS glass also typically contains a sufficient amount of elutable fluoride ions so that the hardened composition will have cariostatic properties.

The glass can be made from a melt containing fluoride, silica, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Suitable FAS glasses will be familiar to those skilled in the art, and are available from a wide variety of commercial sources, and many are found in currently available glass ionomer cements such as those commercially available under the trade designations Ketac™-Molar or Ketac™-Fil Plus (3M ESPE Dental), and FUJI™ IX (G-C Dental Industrial Corp., Tokyo, Japan).

Fluoroaluminosilicate glasses can be prepared by fusing mixtures of silica, alumina, cryolite and fluorite.

Useful acid-reactive inorganic glasses can also be characterized by the Si/Al ratio. Fillers having a Si/Al ratio (by wt.-%) of below 1.5 or 1.4 or 1.3 were found to be useful. Suitable acid-reactive inorganic fillers are also commercially available from e.g. Schott AG (Germany) or Specialty Glass (US).

Mixtures of acid-reactive inorganic fillers can be used, if desired.

The acid-reactive inorganic filler is typically present in the following amount:
Lower limit: at least 80 or at least 90 or at least 95 wt.-%;
Upper limit: at most 100 or at most 99 or at most 98 wt.-%;
Range: from 80 to 100 or from 90 to 99 or from 95 to 98 wt.-%;
wt.-% with respect to the weight of the Powder Part P.

If the amount of the acid-reactive inorganic filler is too low, a suitable paste cannot be obtained by mixing the respective pastes of the kit of parts described in the present text. Further, the mechanical properties might become inferior.

The kit of parts described in the present text comprises a Liquid Part L.
Liquid Part L contains water.
Water is typically present in the following amount:
Lower limit: at least 7 or at least 9 or at least 11 wt.-%;
Upper limit: at most 20 or at most 19 or at most 18 wt.-%;
Range: from 7 to 20 or from 9 to 19 or from 11 to 18 wt.-%;
wt.-% with respect to the weight of Liquid Part L.

Liquid Part L also contains a polyacid.

The nature and structure of the polyacid is not particularly limited, either, unless the desired result cannot be achieved. However, the polyacid should have a molecular weight sufficient to provide good storage, handling, and mixing properties, as well as to yield good material properties in the glass ionomer material.

According to one embodiment, the polyacid can be characterized by at least one or more or all of the following parameters:
Being a solid (at 23° C.);
Molecular weight (Mw): from about 2,000 to about 250,000 or from about 5,000 to about 100,000 (evaluated against a polyacrylic acid sodium salt standard using gel permeation chromatography).

If the molecular weight of the polyacid is too high, obtaining a workable consistency of the obtained paste when mixing the compositions contained in the kit of parts described in the present text might become difficult. Further, preparation of the compositions might become difficult. In addition, the obtained mixture or composition might become too sticky (i.e. adheres to the dental instrument used for application).

If the molecular weight of the polyacid is too low, the viscosity of the obtained paste is supposed to become too low and the mechanical properties of the final product inferior.

Typically, the polyacid is a polymer having a plurality of acidic repeating units.

The polyacid to be used for the cement composition described in the present text is substantially free of polymerizable groups.

The polyacid need not be entirely water soluble, but typically it is at least sufficiently water-miscible so that it does not undergo substantial sedimentation when combined with other aqueous components.

The polyacid is hardenable in the presence of, for example, an acid-reactive inorganic filler and water, but does not contain ethylenically unsaturated groups.

That is, the polyacid it is a polymer obtained by polymerising an unsaturated acid. However, due to the production process, a polyacid might still contain unavoidable traces of free monomers (e.g. up to 1 or 0.5 or 0.3 wt.-% with respect to the amount of monomers used).

Typically, the unsaturated acid is an oxyacid (i.e. an oxygen containing acid) of carbon, sulfur, phosphorous, or boron. More typically, it is an oxyacid of carbon.

Suitable polyacids include, for example, polyalkenoic acids such as homopolymers and copolymers of unsaturated mono-, di-, or tricarboxylic acids.

Polyalkenoic acids can be prepared by the homopolymerization and copolymerization of unsaturated aliphatic carboxylic acids, e.g., acrylic acid, methacrylic acid, itaconic acid, maleic acid, glutaconic acid, aconitic acid, citraconic acid, mesaconic acid, fumaric acid, and tiglic acid.

Suitable polyacids also include alternating copolymers of maleic acid and ethylene (e.g. in a molar one to one ratio).

Suitable polyacids are also described in the following documents: U.S. Pat. No. 4,209,434 (Wilson et al.), U.S. Pat. No. 4,360,605 (Schmitt et al.). The content of these documents with respect to the description of the polyacid is herewith incorporated by reference.

Suitable polyacids are also included as aqueous solutions in the liquid components of commercially available products from e.g. 3M ESPE (e.g. Ketac™ Fil Plus Handmix) or GC Company (e.g. Fuji™ IX GP Handmix).

The amount of polyacid should be sufficient to react with the acid-reactive filler and to provide an ionomer composition with desirable hardening properties.

The polyacid is typically present in the following amount:
Lower limit: at least 3 or at least 5 or at least 10 wt.-%;
Upper limit: at most 70 or at most 60 or at most 50 wt.-%;
Range: from 3 to 70 or from 5 to 60 or from 10 to 50 wt.-%;
wt.-% with respect to the weight of Liquid Part L.

If the amount of the polyacid is too high, obtaining a workable consistency of the obtained paste when mixing the compositions contained in the kit of parts described in the present text might become difficult. Further, preparation of the compositions might become difficult. In addition, the obtained mixture or composition might become too sticky (i.e. adheres to the dental instrument used for application).

If the amount of the polyacid is too low, obtaining a workable consistency of the obtained paste when mixing the compositions contained in the kit of parts described in the present text might become difficult, either. Further, it will become difficult to achieve the desired mechanical properties.

If desired, polyacid can also be present in the Powder Part P.

Liquid Part L contains a complexing agent or chelating agent.

The nature and structure of the complexing or chelating agent is not particularly limited, either unless the desired result cannot be achieved.

The complexing or chelating agent can be characterized by at least one or more or all of the following parameters:
Solubility: soluble in water (at least 50 g/l water at 23° C.);
Molecular weight: from 50 to 500 g/mol, or from 75 to 300 g/mol.

Specific examples of the complexing or chelating agent include tartaric acid, citric acid, ethylene diamine tetra acetic acid (EDTA), salicylic acid, mellitic acid, dihydroxy tartaric acid, nitrilotriacetic acid (NTA), 2,4 and 2,6 dihydroxybenzoic acid, phosphono carboxylic acids, phosphono succinic acid and mixtures thereof.

Further examples can be found e.g. in U.S. Pat. No. 4,569,954 (Wilson et al.). The content of this document is herewith incorporated by reference.

The complexing or chelating agent is typically added to that part containing the polyacid only, i.e., to Liquid Part L.

The complexing or chelating agent is typically present in the following amount:
Lower limit: at least 0.1 or at least 1.0 or at least 1.5 wt.-%;
Upper limit: at most 12 or at most 10 or at most 8 wt.-%;
Range: from 0.1 to 12 or from 1.0 to 10 or from 1.5 to 8 wt.-%;
wt.-% with respect to the weight of Liquid Part L.

Liquid Part L of the kit of parts described in the present text can also contain solvent(s).

Adding solvent(s) or co-solvent(s) may help to adjust the viscosity and consistency of the composition.

Examples of solvent(s) which can be used include alcohols (e.g. methanol, ethanol, propanol), polyalcohols/polyols (e.g. ethylene glycol, glycerol) and mixtures thereof.

Liquid Part L can be characterized by either, more or all of the following features:
Viscosity: from 1 to 500 Pa*s (28° C.; 10 mm diameter; shear rate: 1 $s^{-1}$);
Density: from 1.1 to 2.0 $g/cm^3$;
pH value of a dispersion of 1 g Liquid Part L and 10 ml water (having an initial pH value of 6) after stirring for 5 min: between 1 and 4.

Either the Liquid Part L or the Powder Part P or the Liquid Part L and the Powder Part P contain non-aggregated nano-sized particles.

According to one embodiment, the Liquid Part L contains non-aggregated nano-sized particles.

Placing the non-aggregated nano-sized particles in the Liquid Part L can be beneficial as this may help to reduce the amount of Powder Part P needed for preparing the desired glass ionomer composition. Thus, a more balanced powder/liquid ratio can be obtained.

According to another embodiment, the non-aggregated nano-sized particles are contained in the Liquid Part L only.

The nature and structure of the non-aggregated nano-sized particles is not particularly limited, either, unless the desired result cannot be achieved.

The non-aggregated nano-sized particles should be non-toxic and suitable for use in the mouth of a human being.

The non-aggregated nano-sized particles can be radiopaque or radiolucent.

The non-aggregated nano-sized particles are typically non-acid reactive. That is, the particles do not cure in a glass ionomer cement reaction, if combined with a polyacid in the presence of water.

According to one embodiment, the non-aggregated nano-sized particles can be characterized by at least one or more or all of the following parameters:
Mean particle size: 5 nm to 500 nm or 5 to 300 nm or 5 to 200 nm
Containing no particles larger than 2 μm;
pH value of a dispersion of 1 g nano-sized particles and 10 ml water (having an initial pH value of 6) after stirring for 5 min: between 4 and 7.

According to a preferred embodiment, the non-aggregated nano-sized particles are characterized by either or all of the following:
a) being based on silica,
b) being non surface treated,
c) being non acid-reactive,
d) having a mean particle size in the range of 5 nm to 150 nm,
e) being present in the Liquid Part L only, and/or
f) being present in an amount of 0.1 to 20 wt.-% or 0.2 to 15 wt.-% with respect to the weight of the whole composition.

For providing a low viscous composition, a combination of the following features is sometimes preferred: a) and d) or a) and f) or a), b) and c) or b), c) and d). Thus, the non-aggregated nano-sized particles described in the present text can be surface-treated or non surface-treated.

According to one embodiment, the non-aggregated nano-sized particles are surface-treated with a surface-treating agent not comprising a reactive moiety, like a (meth)acrylate moiety.

Suitable surface-treating agent not comprising a reactive moiety include silanes with a polyethylene residue, silanes with an alkyl residue (e.g. $C_1$ to $C_{12}$ residue).

Further examples include methyltrimethoxysilane, dimethyldimethoxysilane, phenyltrimethoxysilane, methyltriethoxysilane, dimethyldiethoxysilane, phenyltriethoxysilane, hexyltrimethoxysilane, octyltriethoxysilnae, decyltriethoxysilane, etc.

Using non-aggregated nano-sized particles being surface treated with a surface-treating agent not comprising a reactive moiety may help to prevent agglomeration of the nano-sized particles during storage and/or if contained in the Powder Part P of the kit of parts described in the present text and are thus more storage stable. To achieve this desired effect, a full surface coverage of the particles is usually not necessary or desired. This leaves free hydroxyl groups on the particle surface preserving the hydrophilic nature of the filler.

Alternatively or in addition, using these surface treated particles can be advantageous as the treatment with hydrophilic silanes may further enhance the hydrophilic nature of the filler. This may be beneficial during the production process, if the filler is to be combined with water.

In contrast to this, fillers having been surface treated with surface-treating agents comprising a reactive moiety like a (meth)acrylate moiety are sometimes less stable and may start to polymerize during storage.

Examples of surface treating agents with a reactive moiety are 3-methacryl-oxypropyltrimethoxysilane (MPTS), 8-methacryloyloxyoctyl trimethoxysilane, 9-methacryloyloxynonyl trimethoxysilane, 10-methacryloyloxydecyl trimethoxysilane, 11-methacryloyloxyundecyl trimethoxysilane, 11-methacryloyloxyundecyl dichloromethylsilane, 11-methacryloyloxyundecyl trichlorosilane, 11-methacryloyloxyundecyl dimethoxymethylsilane, 12-methacryloyloxydodecyl trimethoxysilane, 13-methacryloyloxytridecyl trimethoxysilane, and the like.

If the mean particle size of the non-aggregated nano-sized particles is above the range outlined above, the consistency of the finally obtained paste might not be adequate and in addition it might become difficult to obtain the desired mechanical properties.

If the mean particle size of the non-aggregated nano-sized particles is below the range outlined above, the desired consistency of the finally obtained paste might not be adequate, either.

Also, if the particles are agglomerated, the consistency of the finally obtained paste might not be adequate or it might become difficult to obtain the desired mechanical properties or both.

Appropriate measurements to ensure that non-aggregated particles are used include TEM of the raw material(s), light scattering of the raw material(s) and intermediate(s), SEM of the mixed and hardened composition.

Since the particle size of the particles used is quite small (below 500 nm), particles resulting from sol-gel syntheses have proven to be in particular useful.

Suitable non-aggregated nano-sized particles are also described in the following documents: US 2005/0252413 A1 (Kangas et al.) and U.S. Pat. No. 7,393,882 (Dong Wu et al.). The content of these documents with respect to the description of the non-aggregated nano-sized particles is herewith incorporated by reference.

It can be beneficial if the non-aggregated nano-sized particles are provided as a dispersion or sol of particles in a liquid (e.g. water). This may allow an easier formulation of the composition.

If the nano-sized particles are provided as an aqueous dispersion or sol, the amount of water in the aqueous dispersion or sol has to be taken into account when the amount of water and filler in the composition is calculated or determined.

According to one embodiment the surface of the non-aggregated nano-sized particles is not surface treated, e.g. with silanes.

In contrast to other nano-sized particles based on titania or zirconia, nano-sized particles based on silica or alumina are preferred.

Examples of suitable non-aggregated nano-sized particles are materials including, but not limited to: non-aggregated silica particles (silica dispersions e.g. from Nalco Chemical Co. (Naperville, Ill.) under the product designation NALCO COLLOIDAL SILICAS e.g. NALCO products #1040, 1042, 1050, 1060, 2327 and 2329; or e.g. from Obermeier, Bad Berleburg, Germany under the trade name Levasil™, including type "50/50%".) and non-aggregated alumina particles.

Mixtures of these non-aggregated nano-sized particles can also be used, if desired.

Nano-sized particles based on titania or zirconia often result in compositions being too opaque, because they tend to agglomerate or precipitate in the system and thus are not suitable to provide aesthetic dental restorations.

The nano-sized particles are typically present in the following amounts:
Lower limit: at least 0.1 or at least 0.2 or at least 1 wt.-%;
Upper limit: at most 50 or at most 40 or at most 30 wt.-%;
Range: from 0.1 to 50 or from 0.2 to 40 or from 1 to 30 wt.-%.
wt.-% with respect to the weight of the whole composition.

Either Powder Part P or Liquid Part L or Powder Part P and Liquid Part L of the kit of parts described in the present text can also contain other non-acid reactive filler(s) being different from the nano-sized particles.

If present, the mean particle size of the non acid-reactive filler is larger than the mean particle size of non-aggregated nano-sized particles.

According to one embodiment, the non acid-reactive filler can be characterized by at least one or more or all of the following parameters:
Mean particle size: about 1 to about 10 µm;
(d10/µm): from 0.2 µm to 2 µm; (d50/µm): from 0.5 µm to 5 µm; (d90/µm) from 1 µm to 15 µm.

Examples of suitable non-acid reactive fillers are naturally occurring or synthetic materials including, but not limited to: quartz; nitrides (e.g., silicon nitride); glasses derived from, e.g., Zr, Sr, Ce, Sb, Sn, Ba, Zn, and Al; borosilicate glass; kaolin; silica particles (e.g. quartz glass or pyrogenic silica of suitable particle size), alumina, titania and zirconia particles.

According to one embodiment, the non-acid reactive filler is selected from quartz, quartz glass, silica, alumina, aluminosilicates and mixtures thereof.

If desired, the surface of the particles of the acid-reactive filler can be surface treated.

Conducting a surface treatment can be beneficial for improving the compatibility of the filler with the other components of the glass ionomer composition.

Suitable surface-treating agents include silanes, e.g. trimethoxysilanes carrying an organic functional group to modify the chemical properties of the particles. Suitable silanes are e.g. silanes to modify the acidic properties (carrying amino groups or carrying carboxylic acid groups) or silanes to modify the hydrophobicity/hydrophilicity (carrying an alkane chain or carrying a polyethylene glycol chain).

If present, the non acid-reactive filler is typically present in the following amounts:
Lower limit: at least 5 or at least 10 or at least 15 wt.-%;
Upper limit: at most 60 or at most 50 or at most 40 wt.-%;
Range: from 5 to 60 or from 10 to 50 or from 15 to 40 wt.-%.
wt.-% with respect to the weight of the whole composition.

Either Powder Part P or Liquid Part L or Powder Part P and Liquid Part L of the kit of parts described in the present text can also contain additive(s).

Additives which might be present include indicator(s), dye(s), pigment(s), viscosity modifier(s), surfactant(s), buffering agent(s), stabilizer(s), preservative agent(s) (e.g., benzoic acid).

If additives are present, the Powder Part P contains only additive(s) which can be provided in powder form as well.

Combination of any of the above additives may also be employed. The selection and amount of any one such additive can be selected by one of skill in the art to accomplish the desired result without undue experimentation.

There is no need for those component(s) to be present, however, if present, the individual component is typically present in an amount of less than 5 wt.-% or less than 3 wt.-% or less than 1 wt.-% with respect to the weight of the respective Parts (L or P). Useful ranges of those component(s) include from 0.01 to 5 wt.-% or from 0.05 to 3 wt.-% or from 0.1 to 1 wt.-%, wt.-% with respect to the weight of the respective Parts (L or P).

Typically, neither Powder Part P nor Liquid Part L of the kit of parts described in the present text contain either of the following components alone or in combination:
a) HEMA in an amount above 1 wt.-% or above 0.5 wt.-%;
b) radically polymerizable component(s) in an amount above 1 wt.-% or above 0.5 wt.-%;

c) initiator component(s) suitable to cure radically polymerizable component(s) or monomer(s) in an amount above 1 wt.-% or above 0.5 wt.-%;
d) inhibitor(s) like methoxyphenol or 3,5-Di-tert-butyl-4-hydroxytoluol in an amount above 1 wt.-% or above 0.5 wt.-%.

Thus, the composition obtained when mixing the powder and liquid part of the kit of parts described in the present text is not a so-called resin-modified glass ionomer cement (RM-GIC) and thus does not contain a curing system suitable for curing radically polymerizable components.

In particular, the cement composition described in the present text does not contain a redox-initiator system or a thermally induced initiator system or a radiation induced initiator system.

In particular the cement composition described in the present text does not contain the following components:
  (a) and (b),
  (b) and (c),
  (a), (b) and (c),
  (b), (c) and (d),
  (a), (b), (c) and (d)
in an amount above 1 wt.-% or above 0.5 wt.-% or above 0.1 wt.-% with respect to the weight of the whole composition.

That is, the cement composition described in the present text is typically essentially free of either of these components alone or in combination.

The glass ionomer composition obtained when mixing Powder Part P and Liquid Part L of the kit of parts described in the present text can typically be characterized as follows:
comprising non-aggregated nano-sized particles in the following amounts:
  Lower limit: at least 0.1 or at least 0.2 or at least 1 wt.-%;
  Upper limit: at most 50 or at most 40 or at most 30 wt.-%;
  Range: from 0.1 to 50 or from 0.2 to 40 or from 1 to 30 wt.-%;
comprising acid-reactive filler in the following amounts:
  Lower limit: at least 30 or at least 40 or at least 50 wt.-%;
  Upper limit: at most 85 or at most 80 or at most 75 wt.-%;
  Range: from 30 to 85 or from 40 to 80 or from 50 to 75 wt.-%;
comprising water in the following amounts:
  Lower limit: at least 6 or at least 8 or at least 10 wt.-%;
  Upper limit: at most 20 or at most 19 or at most 18 wt.-%;
  Range: from 6 to 20 or from 8 to 19 or from 10 to 18 wt.-%;
comprising the polyacid in the following amounts:
  Lower limit: at least 2 or at least 4 or at least 7 wt.-%;
  Upper limit: at most 40 or at most 30 or at most 20 wt.-%;
  Range: from 2 to 40 or from 4 to 30 or from 7 to 20 wt.-%;
comprising complexing agent or chelating agent in the following amounts:
  Lower limit: at least 0.1 or at least 0.5 or at least 1.0 wt.-%;
  Upper limit: at most 10 or at most 8 or at most 6 wt.-%;
  Range: from 0.1 to 10 or from 0.5 to 8 or from 1.0 to 6 wt.-%;
optionally comprising non acid-reactive filler in the following amounts:
  Lower limit: 0 or at least 2 or at least 4 wt.-%;
  Upper limit: at most 40 or at most 35 or at most 30 wt.-%;
  Range: from 0 to 40 or from 2 to 35 or from 4 to 30 wt.-%;
optionally comprising additive(s) in the following amounts:
  Lower limit: 0 or at least 2 or at least 4 wt.-%;
  Upper limit: at most 25 or at most 20 or at most 15 wt.-%;
  Range: from 0 to 25 or from 2 to 20 or from 4 to 15 wt.-%.

With respect to the above amount, the wt.-% refer to the weight of the whole composition obtained when mixing the parts of the kit of parts.

The amount of fillers (non-aggregated nano-sized particles, acid reactive filler and optionally non-acid reactive filler) contained in the composition obtained when mixing Powder Part P and Liquid Part L is typically above 50 or above 55 or above 60 wt.-%.

The water content of the composition obtained when mixing Powder Part P and Liquid Part L is below 20 or below 19 or below 18 or below 17 wt.-%.

A high filler content combined with a low water content typically helps to improve mechanical properties of the hardened composition like compressive strength.

The invention also relates to a composition obtainable or obtained when mixing the components contained in the respective parts of the kit of parts described in the present text.

According to one embodiment the composition obtained or obtainable by mixing the two parts of the kit of parts described in the present text fulfills at least one or more or sometimes all of the following parameters before or during hardening:
  Setting time: within about 5 or 4 or 3 min determined according to EN-ISO 9917-1:2007;
  Working time: within about 4 or 3 or 2 or 1 min determined according to EN-ISO 9917-1:2007;
  Viscosity: 2,000 to 10,000 Pa*s at 28° C. measured 90 sec after start of mixing the components of Powder Part P and Liquid Part L.

If desired, the setting time and curing behaviour can be determined as described in more detail in the Example section below.

The composition described in the present text typically has a sufficient working time allowing the practitioner not only to adequately mix the composition but also to apply the composition to a cavity or the surface of a crown, bridge, root canal or prepared tooth.

Further, the composition described in the present text has an adequate setting time, which is time saving for the practitioner and convenient for the patient.

According to another embodiment the composition obtained or obtainable by mixing the two parts of the kit of parts described in the present text fulfills at least one or more or sometimes all of the following parameters after hardening:
  Flexural strength: above about 20 or above about 25 MPa determined according to EN-ISO 9917-2:2010 with the proviso that for covering the composition a glass slab is used instead of a foil;
  Compressive strength: above about 100 or above about 120 or above about 150 MPa determined according to EN-ISO 9917-1/2007 with the proviso that for covering the composition a glass slab is used instead of a foil.

If desired, these parameters can be determined as described in the Example section below.

Compared to state of the art glass ionomer cement compositions available on the market, the composition described in the present text can easily be mixed and has adequate mechanical properties like compressive and/or flexural strength without affecting other important parameters like setting time.

According to one embodiment, the invention is directed to a kit of parts for preparing a glass ionomer composition for dental use, the kit of parts comprising a Powder Part P and a Liquid Part L, Powder Part P comprising
acid-reactive inorganic filler,
Liquid Part L comprising
water,
complexing agent,
polyacid,
non-aggregated nano-sized particles,
the composition obtained by combining the components of Powder Part P and Liquid
Part L before hardening comprising the components in the following amounts:
non-aggregated nano-sized particles: from 2 to 10 wt.-%,
acid-reactive filler in an amount from 50 to 75 wt.-%,
polyacid: 10 to 20 wt.-%,
complexing agent: 0.5 to 3 wt.-%,
water: 9 to 17 wt.-%,
wt.-% with respect to the weight of the whole composition,
the non-aggregated nano-sized particles being characterized as follows:
based on silica or alumina, preferably on silica,
being non surface treated,
being non acid-reactive,
having a mean particle size in the range of 5 nm to 150 nm and/or
being present in the Liquid Part L only.

According to a further embodiment, the invention is directed to a kit of parts for preparing a glass ionomer composition for dental use, the kit of parts comprising a Powder Part P and a Liquid Part L, Powder Part P comprising
acid-reactive inorganic filler,
Liquid Part L comprising
water,
complexing agent,
polyacid,
non-aggregated nano-sized particles,
the composition obtained by combining the components of Powder Part P and Liquid Part L before hardening comprising the components in the following amounts:
non-aggregated nano-sized particles: from 2 to 10 wt.-%,
acid-reactive filler in an amount from 50 to 75 wt.-%,
polyacid: 10 to 20 wt.-%,
complexing agent: 0.5 to 3 wt.-%,
water: 9 to 17 wt.-%,
wt.-% with respect to the weight of the whole composition,
the non-aggregated nano-sized particles being characterized as follows:
based on silica or alumina, preferably on silica,
being either non surface treated or being surface treated with a surface treating agent not comprising a reactive moiety,
being non acid-reactive,
having a mean particle size in the range of 5 nm to 150 nm and/or
being present in the Liquid Part L only.

The parts of the kit of part described in the present text can be produced by simply mixing the individual components of the respective parts.

If needed, the filler particles can be milled to the desired particle size using equipment known to the skilled person like ball mills.

Mixing can be accomplished either by hand or with a mechanical device like a mixer or kneading machine. The mixing duration can vary depending on the composition and the mixing device and should be sufficiently long to obtain a homogeneous paste.

According to one embodiment, the Liquid Part L of the kit of parts is prepared by providing and adding the respective components in the following order: a) a dispersion of water and non-aggregated nano-sized particles, b) complexing agent, c) polyacid.

Such a sequence was found to be particularly useful as the risk of clogging or settling of individual parts is reduced.

The kit of parts described in the present text can be provided to the practitioner in different embodiments.

The Powder Part and Liquid Part may be contained in separate sealable vessels (e.g. made out of plastic or glass).

For use, the practitioner may take adequate portions of the components from the vessels and mix the portions by hand on a mixing plate.

According to a preferred embodiment, the respective parts are contained in separate compartments of a delivery system.

Thus, the invention is also directed to a device for storing and delivery of the kit of parts described in the present text, the device comprising Compartment A and Compartment B separated from each other during storage and a nozzle connected to either Compartment A or Compartment B, Compartment A containing Powder Part P and Compartment B containing Liquid Part L, wherein Compartment A has a volume in the range of 0.5 to 3 ml or 0.8 to 2 ml and Compartment B has a volume in the range of 0.05 to 1 ml or 0.08 to 0.5 ml.

The mixing ratio of Powder Part P and Liquid Part L is typically from 6:1 to 1:1 with respect to weight, preferably from 4:1 to 1:1.

Other suitable delivery systems are described e.g. in U.S. Pat. No. 6,543,611 B1 (3M ESPE), U.S. Pat. No. 4,941,751 (Muehlbauer), U.S. Pat. No. 5,088,830 (Muehlbauer), U.S. Pat. No. 6,386,872 (Muasa et al.) or EP 0 783 872 A2 (Voco). The content of these references is herewith incorporated by reference.

The composition obtained or obtainable when mixing the respective parts of the kit of parts described in the present text is in particular useful as or for producing a dental luting cement, dental filling material, dental core build up material, dental liner or as dental root channel filling material.

A typical application comprises the following steps:
a) mixing Powder Part P and Liquid Part L to obtain a hardenable composition,
b) applying the hardenable composition to the surface of hard dental tissue,
c) letting the hardening composition harden.

The kit of parts described in the present text typically contains in addition an instruction for use.

The instruction for use typically contains hints how to store the kit of parts, mix the respective parts of the kit of parts and/or how to apply the composition obtained by mixing the parts to the surface of hard dental tissue.

The invention is also directed to a method of using nano-particles as described in present text for reducing the viscosity of a glass ionomer composition, in particular a glass ionomer composition obtainable or obtained by mixing the components contained in Powder Part P and Liquid Part L as described in the present text.

All components used in the dental composition of the invention should be sufficiently biocompatible, that is, the composition should not produce a toxic, injurious, or immunological response in living tissue.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

The following examples are given to illustrate, but not limit, the scope of this invention.

EXAMPLES

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 1013 mbar).

Methods

Density

The density of the composition(s) was measured by filling the composition into a container of defined volume and by weighing the container with and without composition. The weight difference divided by the defined volume yields the density of the composition. It was taken care that during filling of the container the inclusion of air bubbles was avoided or at least minimized.

Viscosity

The viscosity of the composition was measured with a Physica MCR 300 rheometer from Anton Paar. The measurement was performed in a rotating disc on disc setup with the diameter being 10 mm. The temperature was set to 28° C., the gap to 2 mm and the shear rate to 1 $s^{-1}$.

More material than needed to fill the measurement gap was used and the excess material was not removed before the measurement. It was taken care that the excess material did not come in contact with the sides of the rotating 10 mm cylinder.

Five values taken from 31 to 35 seconds into the measurement were averaged. This time frame lies 88 to 92 seconds after the start of the mixing procedure and represents the value for the viscosity 90 seconds after start of the mixing procedure. Repeat determination was done for all samples.

pH Value

The pH value of the solutions and dispersions was measured with a pH electrode.

Compressive Strength (CS)

Measurement of the compressive strength was carried out according to the EN-ISO 9917-1:2007 with the proviso that for covering the composition a glass slab is used instead of a foil.

Cylindrical specimens with a diameter of 4 mm and a height of 6 mm were used. Specimens of the materials were prepared at room temperature and 50% relative humidity using split moulds. The moulds were placed on microscope slides and thoroughly filled with the mixed material to avoid incorporation of air bubbles. The filled moulds were immediately covered with another glass slab and fixed in a screw clamp with slight pressure to extrude excess material. The whole assembly was stored at 36° C. and at least 95% relative humidity. 1 h after start of mixing the specimens were removed from the moulds and immediately placed in water at 36° C. 6 specimens were prepared for each material. Materials were measured 24 h after start of mixing. The exact diameter of each specimen was measured prior to the measurement. The strength of the specimen was measured by applying a compressive load using a Zwick universal testing machine (Zwick GmbH & Co. KG, Ulm, Germany) operating at a crosshead speed of 1 mm/min. Results were reported as an average of 6 replications.

Flexural Strength (FS)

Flexural strength was measured based on EN ISO 9917-2:2010 with the proviso that for covering the composition a glass slab is used instead of a foil;

The specimens were prepared as described for the compressive strength test above, except that rectangular-shaped split moulds with dimensions 25 mm×2 mm×2 mm were used to prepare the samples. The specimens were subjected to a 3 point bend on supports 20 mm apart at a crosshead speed of 1 mm/min.

Particle Size (Suitable for Micro-Sized Particles of Non Acid-Reactive Filler and Acid Reactive Filler)

If desired, the particle size distribution including the mean particle size can be determined with a Cilas 1064 (FA. Quantacrome) particle size detection device. During the measurement, ultrasonic was used to accurately disperse the sample.

Particle Size (Suitable for Nano-Sized Particles)

If desired, particle size measurements can be made using a light scattering particle sizer equipped with a red laser having a 633 nm wavelength of light (obtained under the trade designation "ZETA SIZER—Nano Series, Model ZEN3600" from Malvern Instruments Inc., Westborough, Mass.). Each sample is analyzed in a one-centimeter square polystyrene sample cuvette. The sample is diluted 1:100, e.g. 1 g of sample was given to 100 g of de-ionized water and mixed. The sample cuvette is filled with about 1 gram of diluted sample. The sample cuvette is then placed in the instrument and equilibrated at 25° C. The instrument parameters are set as follows: dispersant refractive index 1.330, dispersant viscosity 0.8872 mPa*s, material refractive index 1.43, and material absorption value 0.00 units. The automatic size-measurement procedure is then run. The instrument automatically adjusts the laser-beam position and attenuator setting to obtain the best measurement of particle size.

The light scattering particle-sizer illuminated the sample with a laser and analyzed the intensity fluctuations of the light scattered from the particles at an angle of 173 degrees. The method of Photon Correlation Spectroscopy (PCS) is used by the instrument to calculate the particle size. PCS uses the fluctuating light intensity to measure Brownian motion of the particles in the liquid. The particle size is then calculated to be the diameter of sphere that moves at the measured speed.

The intensity of the light scattered by the particle is proportional to the sixth power of the particle diameter. The Z-average size or cumulant mean is a mean calculated from the intensity distribution and the calculation is based on assumptions that the particles are mono-modal, mono-disperse, and spherical. Related functions calculated from the fluctuating light intensity are the Intensity Distribution and its mean. The mean of the Intensity Distribution is calculated based on the assumption that the particles are spherical. Both the Z-average size and the Intensity Distribution mean are more sensitive to larger particles than smaller ones.

The Volume Distribution gives the percentage of the total volume of particles corresponding to particles in a given size range. The volume-average size is the size of a particle that corresponds to the mean of the Volume Distribution. Since the volume of a particle is proportional to the third power of the diameter, this distribution is less sensitive to larger particles than the Z-average size. Thus, the volume-average will typically be a smaller value than the Z-average size.

In the scope of this document the Z-average size is referred to as "mean particle size".

Molecular Weight

If desired, the molecular weight (Mw) can be determined by gel permeation chromatography (GPC) against a polyacrylic acid sodium salt standard.

In particular the following equipment was found to be useful: PSS SECurity GPC System equipped with 2*PSS Suprema 3000A, 8*300 mm, 10 μm columns; eluent: 84 mM Na2HPO4+200 ppm NaN3; flux rate: 1 ml/min.

Working Time (ta) and Setting Time (te)

If desired, the setting behaviour of the prepared glass ionomer cement composition can be determined using a Physica MCR 301 Rheometer (Anton Paar) applying the following parameters:

Oscillating measurement with 8 mm disc on disc set-up; gap 0.75 mm; deformation 1.75%; frequency: 1.25 HZ; temperature: 28° C.

The loss angle (in German: "Verlustwinkel") is recorded over time and the maximum (ta) and the minimum (te) of the graph determined. The average of two measurements with respect to the maximum and the minimum is given in min:sec.

Materials

TABLE 1

| Name | Description |
| --- | --- |
| Levasil ™ 50/50% | Nano-sized particles (from Obermeier); dispersion of silica particles in water at about 50 wt.-% solids; mean particle size of silica particles: 114 nm |
| Aerosil ™ Ox50 | Nano-sized particles (from Evonik); fumed silica particles; BET surface according to manufacturer data sheet: 35-65 $m^2/g$ |
| Nalco ™ 2326 | Non-aggregated nano-sized particles (from Nalco); dispersion of silica particles in water at about 15 wt.-% solids; mean particle size of silica particles: 5 nm |
| Silquest ™ A1230 | Surface treating agent (from Momentive); silane with polyethylene glycol (PEG) residue |
| isooctyltrimethoxysilane | Surface treating agent (from Gelest); silane with isooctyl residue |
| methyltrimethoxysilane | Surface treating agent (from Gelest); silane with methyl residue |
| ionomer glass powder (IGP) | Acid-reactive filler; powder component of Ketac ™ Molar ART (from 3M ESPE Dental); mean particle size: 3.84 μm, d10: 0.87 μm, d50: 2.73 μm, d90: 8.80 μm. |
| tartaric acid (TA) | Complexing or chelating agent |
| Polyacid (PA) | Polyacid; acrylic acid/maleic acid co-polymer (1:1 co-polymer), Mw = 20,000, offered in aqueous solution as liquid component of Ketac ™ Molar (from 3M ESPE Dental) |
| silane (X-12-967C) | Surface treating agent (from Shin-Etsu); silane with succinic acid anhydride residue |

Liquid Composition 1

A Liquid Composition #1 containing 0.73 g de-ionized water, 0.17 g tartaric acid, 1.16 g polyacid and 0.34 g Levasil™ 50/50 (containing 50% water and 50% silica particles without surface-treatment) was prepared. A homogeneous mixture was obtained by mixing with a magnetic stirrer.

The viscosity of Liquid Composition 1 was determined in the same way as the viscosity of the mixed pastes: 17 Pa*s.

Liquid Composition 2

A Liquid Composition #2 containing 0.21 g tartaric acid, 1.38 g polyacid and 2.68 g Levasil™ 50/50 (containing 50% water and 50% silica particles without surface-treatment) was prepared. A homogeneous mixture was obtained by mixing with a magnetic stirrer. Under continued stirring, 0.27 g of water were evaporated at room temperature, simply by opening the lid of the mixing vessel.

The viscosity of Liquid Composition 2 was determined in the same way as the viscosity of the mixed pastes: 123 Pa*s.

Liquid Composition 3

A Liquid Composition #3 was prepared the following way:

The silane (X-12-967C) was hydrolysed with ammonia solution as a catalyst. The hydrolysis took place at a pH value of 9. The silanization was performed with 0.236 mmol silane per 1 g of silica in the Levasil™ 50/50%. The solvent was ethanol with a ratio of ethanol to silica 50:50 by weight. The silanization was conducted for 16 hours at 70° C. The mixture was dried in a rotary evaporator. The dry substance was sieved (500 μm) and the silanization was fixed in a rotary evaporator (standard pressure, 100° C., 1 hour).

The Liquid Composition #3 containing 2.70 g de-ionized water, 0.51 g tartaric acid, 3.48 g polyacid and 0.51 g silica particles (surface-treated with X-12-967C) was prepared. A homogeneous mixture was obtained by mixing with a magnetic stirrer.

The viscosity of Liquid Composition 3 was determined in the same way as the viscosity of the mixed pastes: 12 Pa*s.

Powder Composition 4

A Powder Composition #4 was prepared in the following way:

100.0 g Nalco™ 2326 (16.5% solids) was combined with 5.07 g isooctyltrimethoxysilane, 3.61 Silquest™ A1230, 90 g of ethanol and 23 g of methanol in a three neck round bottom flask equipped with an overhead mechanical stirrer and a water cooled condenser. The components were stirred while being heated to 80° C. overnight. The surface modified particles were then dried at 150° C. in a vented oven until dry. The nanoparticles were ground with a mortar and pestle and used without further purification.

Appropriate amounts of the materials (50 g total) (nanoparticles at 0.5 wt.-% and ionomer glass powder (Ketac™ Molar ART powder at 99.5 wt.-%) were placed in a plastic cup and mixed using a FlackTek DAC 150FVZ Speedmixer (FlackTek, Inc, Landrum, S. C., USA). The samples were each mixed for 60 seconds at 3,000 rpm.

Powder Composition 5

A Powder Composition #5 was prepared in the following way:

100 g Nalco™2326 (16.5% soilds) was combined with 2.14 g isooctyltrimethoxysilane, 0.84 g methyltrimethoxysilane, 90 g ethanol and 23 g methanol. The reaction time/temperature and workup is the same as described with respect to Powder Composition #4.

Liquid Composition 6

A Liquid Composition #6 containing 4.03 g de-ionized water, 0.78 g tartaric acid and 5.19 g polyacid was prepared. A homogeneous mixture was obtained by mixing with a magnetic stirrer.

The viscosity of Liquid Composition 6 was determined in the same way as the viscosity of the mixed pastes: 11 Pa*s.

Liquid Composition 7

A Liquid Composition #1 containing 2.70 g de-ionized water, 0.51 g tartaric acid, 3.48 g polyacid and 0.51 g Aerosil™ Ox50 (fumed silica particles without surface-treatment) was prepared. A homogeneous mixture was obtained by mixing with a magnetic stirrer.

The viscosity of Liquid Composition 1 was determined in the same way as the viscosity of the mixed pastes: 48 Pa*s.

Inventive Example 1

Liquid Composition #1 was mixed with ionomer glass powder (Ketac™ Molar ART powder) at a weight ratio of 1:2.5 with a spatula.

Inventive Example 2

Liquid Composition #2 was mixed ionomer glass powder (Ketac™ Molar ART powder) at a weight ratio of 1:1.5 with a spatula.

Inventive Example 3

Liquid Composition #3 was mixed with ionomer glass powder (Ketac™ Molar ART powder) at a weight ratio of 1:2.5 with a spatula.

Inventive Example 4

Liquid Composition #6 was mixed with Powder Composition #4 at a weight ratio of 1:2.76 with a spatula.

Inventive Example 5

Polyacid Composition #6 was mixed with Powder Composition #5 at a weight ratio of 1:2.76 with a spatula.

Comparative Example 6

Liquid Composition #6 was mixed with ionomer glass powder (Ketac™ Molar ART powder) at a weight ratio of 1:2.76 with a spatula.

Comparative Example 7

Liquid Composition #7 was mixed with ionomer glass powder (Ketac™ Molar ART powder) at a weight ratio of 1:2.5 with a spatula.

The viscosity of the obtained pastes was determined. In addition the compressive strength and flexural strength of the hardened composition was determined.
Compositions and Results:

The examples were designed to keep the amounts of tartaric acid, polyacid and water in the mixed compositions constant, as the amount of water may have an influence on the viscosity of the mixed paste(s). The amount of nano-particles is subtracted from the amount of ionomer glass.

What can be seen is that the addition of even small amounts of non-aggregated nano sized inorganic particles results in compositions having a lower viscosity than the composition of Comparative Example 6 with no such particles. A low viscosity of the mixed paste indicates beneficial (hand) mixing properties.

The composition of Comparative Example 7 with aggregated particles of fumed silica has good mechanical values, but the miscibility was insufficient and the viscosity of the mixed paste was too high to be measured with the chosen measurement setup.

The invention claimed is:

1. A kit of parts for preparing a glass ionomer composition for dental use,
the kit of parts comprising a Powder Part P and a Liquid Part L,
Powder Part P comprising:
    acid-reactive inorganic filler,
Liquid Part L comprising:
    water,
    complexing or chelating agent,
    polyacid,
either the Powder Part P or the Liquid Part L or the Powder Part P and the Liquid Part L comprising non-aggregated nano-sized particles based on silica or alumina, the composition obtained by combining the components of Powder Part P and Liquid Part L before hardening comprising the components in the following amounts:
    non-aggregated nano-sized particles having a mean particle size in the range of 5 nm to 500 nm from 0.1 to 15 wt.-%,
    acid-reactive filler in an amount from 50 to 75 wt.-%,
    polyacid: 7 to 20 wt.-%,
    complexing agent: 0.5 to 3 wt.-%,
    water: 5 to 18 wt.-%,
wt.-% with respect to the weight of the whole composition.

2. The kit of parts of claim 1, Liquid Part L being characterized by at least one or more of the following parameters:
    viscosity: from 1 to 500 Pa*s at 28° C., measured at a shear rate of 1 s$^{-1}$;

TABLE 2

|  | water [wt.-%] | TA [wt.-%] | PA [wt.-%] | nano-particles [wt.-%] | IGP [wt.-%] | viscosity [Pa*s] | CS [MPa] | FS [Mpa] |
| --- | --- | --- | --- | --- | --- | --- | --- | --- |
| I.E. 1 | 10.7 | 2.0 | 13.8 | 2.0 | 71.5 | 5,200 | 264 | 53 |
| I.E. 2 | 10.7 | 2.1 | 13.8 | 13.4 | 60.0 | 2,300 | 241 | 47 |
| I.E. 3 | 10.7 | 2.0 | 13.8 | 2.0 | 71.5 | 9,600 | 257 | 35 |
| I.E. 4 | 10.7 | 2.1 | 13.8 | 0.4 | 73.0 | 5,200 | 271 | 46 |
| I.E. 5 | 10.7 | 2.1 | 13.8 | 0.4 | 73.0 | 4,600 | 259 | 46 |
| C.E. 6 | 10.7 | 2.1 | 13.8 | 0.0 | 73.4 | 13,600 | 251 | 45 |
| C.E. 7 | 10.7 | 2.0 | 13.8 | 2.0 | 71.5 | — | 286 | 43 |

I.E. = Inventive Example;
C.E. = Comparative Example density: from 1.1 to 2.0 g/cm$^3$;
pH value of a dispersion of 1 g Liquid Part L and 10 ml water (having an initial pH value of 6) after stirring for 5 min: between 1 and 4.

3. The kit of parts of claim 1, the ratio of Powder Part P to Liquid Part L being from 4:1 to 1:1 with respect to weight.

4. The kit of parts of claim 1, the non-aggregated nano-sized particles being characterized by the following feature:
pH value of a dispersion of 1 g nano-sized particles and 10 ml water (having an initial pH value of 6) after stirring for 5 min: between 4 and 7.

5. The kit of parts of claim 1, the non-aggregated nano-sized particles being further characterized as follows:
being based on silica,
being non surface treated,
being non acid-reactive,
being present in the Liquid Part L only, and/or
being present in an amount of 2 to 10 wt.-% with respect to the weight of the whole composition.

6. The kit of parts of claim 1, the acid-reactive filler being characterized by at least one or more of the following features:
pH value of a dispersion of 1 g filler and 10 ml water (having an initial pH value of 6) after stirring for 5 min: between 6 and 10;
having a mean particle size in the range of 3 to 10 μm.

7. The kit of parts of claim 1, the acid reactive filler being selected from basic metal oxides, metal hydroxides, hydroxyapatite, aluminosilicate glasses, fluoroaluminosilicate glasses, glasses having a Si/Al ratio by wt.-% of below 1.5 and mixtures thereof.

8. The kit of parts of claim 1, the polyacid having a molecular weight (Mw) from 2,000 to 250,000 evaluated against a polyacrylic acid sodium salt standard using gel permeation chromatography.

9. The kit of parts of claim 1, the complexing or chelating agent being selected from tartaric acid, citric acid, ethylene diamine tetra acetic acid, salicylic acid, mellitic acid, dihydroxy tartaric acid, nitrilotriacetic acid, 2,4 and 2,6 dihydroxybenzoic acid, phosphono carboxylic acids, phosphono succinic acid and mixtures thereof.

10. The kit of parts of claim 1, not comprising at least one, more or all of the following components:
non-aggregated nano-sized particles based on titania in an amount above 1 wt.-%;
non-aggregated nano-sized particles based on zirconia in an amount above 1 wt.-%;
radically polymerizable component(s) in an amount above 1 wt.-%;
initiator component(s) suitable to cure polymerizable component(s) in an amount above 1 wt.-%;
inhibitor(s) in an amount above 1 wt.-%;
wt.-% with respect to the weight of the whole composition.

11. A composition obtained by combining the components contained in Powder Part P and Liquid Part L of the kit of parts of claim 1, the composition being characterized by the following parameter before hardening:
Viscosity: less than 10,000 Pa*s at 28° C. measured at a shear rate of 1 s$^{-1}$ and 90 sec after start of mixing the components of Powder Part P and Liquid Part L.

12. A composition obtained by combining the components contained in Powder Part P and Liquid Part L of the kit of parts of claim 1, the composition being characterized by at least one, more or all of the following parameters after hardening:
Flexural strength: above 20 MPa determined according to EN-ISO 9917-2:2010;
Compressive strength: above 100 MPa determined according to EN-ISO 9917-1/2007.

13. A dental luting cement, dental filling material, dental core build up material, dental liner or dental root channel filling prepared from the composition of claim 12.

14. A delivery system comprising Compartment A and Compartment B separated from each other during storage and a nozzle connected to either Compartment A or Compartment B, Compartment A containing Powder Part P and Compartment B containing Liquid Part L, the delivery system having the shape of a dental capsule, wherein Compartment A has a volume in the range of 0.5 to 3 ml and Compartment B has a volume in the range of 0.05 to 1 ml, wherein Powder Part P and Liquid Part L are as defined in claim 1.

15. A composition obtained by mixing the components of a Powder Part P and a Liquid Part L of claim 1, wherein the non-aggregated nanoparticles function to reduce the viscosity of the composition.

* * * * *